United States Patent [19]

Lemaire

[11] Patent Number: 5,698,791

[45] Date of Patent: Dec. 16, 1997

[54] METHOD AND DEVICE FOR SEPARATING AND FOR MEASURING THE VOLUME OF THE DIFFERENT PHASES OF A MIXTURE OF FLUIDS

[75] Inventor: Christian Lemaire, Nanterre, France

[73] Assignee: Institut Francais du Petrole, Rueil-Malmaison, France

[21] Appl. No.: 575,037

[22] Filed: Dec. 19, 1995

[30] Foreign Application Priority Data

Dec. 19, 1994 [FR] France ..................... 94 15377

[51] Int. Cl.⁶ ........................................ G02F 1/74
[52] U.S. Cl. ........................................ 73/861.04
[58] Field of Search ............. 73/861.04, 0, 861.03, 73/38, 61.47

[56] References Cited

U.S. PATENT DOCUMENTS

| | | | |
|---|---|---|---|
| 3,009,359 | 11/1961 | Hubby | 73/61.47 |
| 4,487,056 | 12/1984 | Wiley . | |
| 4,672,840 | 6/1987 | Cullick | 73/38 |
| 4,679,421 | 7/1987 | Barree . | |
| 4,856,344 | 8/1989 | Hunt | 73/861.04 |
| 4,868,751 | 9/1989 | Dogru et al. . | |
| 5,069,065 | 12/1991 | Sprunt et al. . | |
| 5,086,643 | 2/1992 | Marek | 73/38 |
| 5,211,842 | 5/1993 | Tuss et al. | 73/861.04 |

FOREIGN PATENT DOCUMENTS 2 595 464  9/1987  France .

Primary Examiner—Richard Chilcot
Assistant Examiner—Jewel V. Artis
Attorney, Agent, or Firm—Antonelli,Terry, Stout, & Kraus, LLP

[57] ABSTRACT

Volumes of different constitutive phases of a multiphase mixture contained in a vessel are measured after vertical stratification, mainly by comparing by two differential pressure detectors, the pressure generated by three fluid columns, one being totally filled with at least one of the fluids (a liquid phase for example topped by a gas phase), a second one with at least two of the fluids (one liquid phase for example topped by the same gas phase). The vessel can be, for example, an elongated column with a calibrated section arranged vertically and provided with pressure taps at three distinct points of the height thereof which taps communicate with detectors by appropriate fine lines. A processing set combines the pressure measurements in order to obtain the respective volumes of the phases. This method can be used for volume measurements in various vessels; notably in chemical engineering facilities and to conduct tests on porous geographic samples saturated with a multiphase mixture.

5 Claims, 1 Drawing Sheet

METHOD AND DEVICE FOR SEPARATING AND FOR MEASURING THE VOLUME OF THE DIFFERENT PHASES OF A MIXTURE OF FLUIDS

FIELD OF THE INVENTION

The present invention relates to a method and to a device for separating and for measuring the volume of the different phases of a multiphase mixture.

The method according to the invention is generally suited for measuring volumes in all sorts of vessels intended for storing multiphase products or substances. It can be, for example, tanks used for the storage or the transportation of hydrocarbons, columns, fermenting tanks or other vessels used in chemical engineering, etc.

The method according to the invention can be applied notably within the scope of continuous tests on samples of porous materials and notably of geologic samples taken in formations that contain or that can contain hydrocarbons. It allows to separate and to measure the volume of the different phases of multiphase mixtures that are obtained during the tests. It is described hereafter by way of example within the particular scope of such an application.

BACKGROUND OF THE INVENTION

The knowledge that can be acquired concerning various petrophysical parameters of rocks during drainage or imbibition phases can be used for example for selecting the most appropriate fluid for displacing the petroleum hydrocarbons they contain and for improving thereby the efficiency of oil enhanced recovery processes in a reservoir.

It is known to determine for example the saturation and the wettability of rocks with respect to fluids such as water (generally in the form of brine), oil and possibly a gas phase that can be contained therein. To that effect, rock drainage phases are carried out, i.e. a displacement of fluids intended to decrease the water saturation, followed by imbibition phases which, on the contrary, are intended to increase its water saturation (Sw). The capillary pressure can thus be measured at a point of a porous sample in the presence of water and oil in the continuous phase, which is defined, as it is well known, as the difference Pc at equilibrium between the pressure P(oil) and the pressure P(water) of water. Devices allowing petrophysical parameters of rocks to be measured are described for example in the patent applications FR-2,603,040, EN-93/09,481 or EN-94/10,783 or in patents U.S. Pat. Nos. 4,868,751 or 5,069,065.

SUMMARY OF THE INVENTION

The method according to the invention is suited for determining the volume of each constituent of a mixture of fluids having different densities which is contained in a vessel.

It is characterized in that the respective volumes of the mixture constituents are determined from the values measured by two pressure detectors, pressures generated by two columns of equal height, one being totally filled with two of the fluids (a liquid phase for example topped by a gas phase), and the other with the three fluids (two liquid phases for example topped by the same gas phase), and the measured pressure values are combined to obtain the respective volumes of the constituents.

The method according to the invention allows the physical characteristics of a sample of porous materials saturated with a (two-phase or three-phase) mixture of fluids having different densities to be continuously tested by means of measurements performed on the fluids that are progressively drained out of the sample and collected in an elongated phase separator comprising a column with a calibrated inner section arranged so as to obtain a natural decantation of the different phases.

It is characterized in that one measures a first pressure difference and a second pressure difference between the pressure prevailing at an intermediate height of the column and respectively the pressure prevailing near the base of the column and the pressure prevailing near the top of the column, and physical characteristics of the sample linked to the volumes of the expelled fluids are determined from these measured pressure differences.

The determination of the physical characteristics of the sample is performed for example by combining the values of these two pressure differences so as to obtain the respective volumes of the liquid phases of the expelled mixture, as well as the respective saturations of the sample with respect to the fluids by comparison of these respective volumes with the known volume of the pores of the sample.

The device according to the invention is characterized in that it comprises an elongated phase separator intended to collect the mixture of fluids expelled from the sample, this separator comprising a column with a calibrated inner section arranged so as to obtain a vertical layering of the different phases, a first means for measuring the pressure difference prevailing between a measuring point near the base of the column and an intermediate measuring point at an intermediate height of the column, and a second means for measuring the pressure difference prevailing between this intermediate measuring point and another measuring point near the top of the column, and means (such as a programmed processing set for example) for combining the signals delivered by these two pressure measuring means in response to the differences measured, in order to determine physical characteristics of the sample linked to the volumes of the expelled fluids.

The first and the second measuring means can be connected to the intermediate point of the column by a line that is either exterior or interior to the column.

With the method and the device according to the invention, continuous drainage or imbibition operations can be achieved automatically, and volume and saturation measurements can be obtained continuously with great precision.

BRIEF DESCRIPTION OF THE DRAWINGS

Other features and advantages of the method and of the device according to the invention will be clear from reading the description hereafter of an embodiment given by way of non limitative example, with reference to the accompanying drawings in which.

DESCRIPTION OF THE PREFERRED EMBODIMENTS

Figure 1:
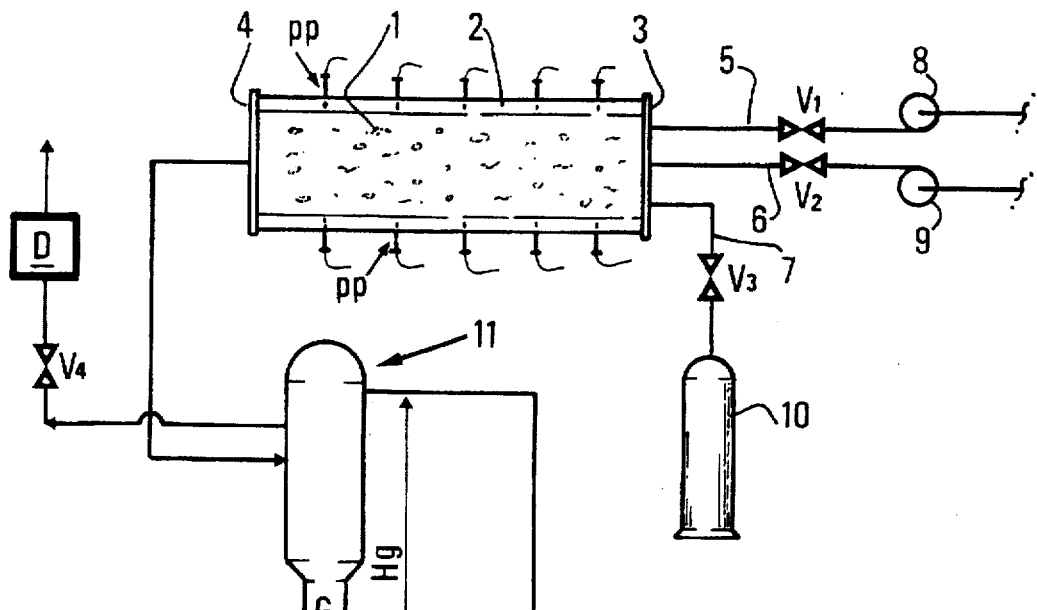
FIG. 1 diagrammatically shows an implementation of the method using a phase separation column, pressure detection means and a pressure difference data processing set.

The method according to the invention can be implemented for example with the device schematized in FIG. 1, described hereafter by way of non limitative example.

The sample bar 1 to be tested is coated for example with a resin sheath (notably araldite). Two end plates 3, 4 lean directly against the end walls of the bar at the ends of the sheath. The first plate 3 is provided with bores intended for the connection of pipes 5, 6, 7 communicating by means of valves V1, V2, V3 respectively with a water injection pump 8, an oil injection pump 9 and a cylinder 10 containing pressurized gas.

Selective pressure taps PP with semipermeable membranes such as those described for example in the parallel patent application Ser. No. 575,042 filed Dec. 19, 1995 can also be inserted through the sheath in different places along the sample, so as to measure selectively the pressures of the different phases in the sample.

The device further comprises a phase separator 11 consisting of an elongated transparent column with a well-calibrated inner section. A line 12 provided with a control valve V4 communicates the upper part of the column 9 with the opposite plate 4.

The column of separator 11 comprises, in the intermediate part thereof between its base and its top, a first port for the connection of an outer line 13 connected to a first inlet of respectively a first differential pressure detector 14 and a second differential pressure detector 15. Two other ports are provided respectively near the base and near the top of column where two other lines 16, 17 connected to the second inlet of respectively the two pressure detectors 14, 15 are connected. An upper port controlled by another valve V5 allows the gas phase to be transferred towards a flowmeter Q or possibly to be discharged out of the separator.

The measuring signals delivered by the two differential pressure detectors 14, 15 are applied to an acquisition input of a processor 18 programmed to lo perform the follow-up of the tests as described hereafter, this processor being connected to a control console 19.

Figure 2:
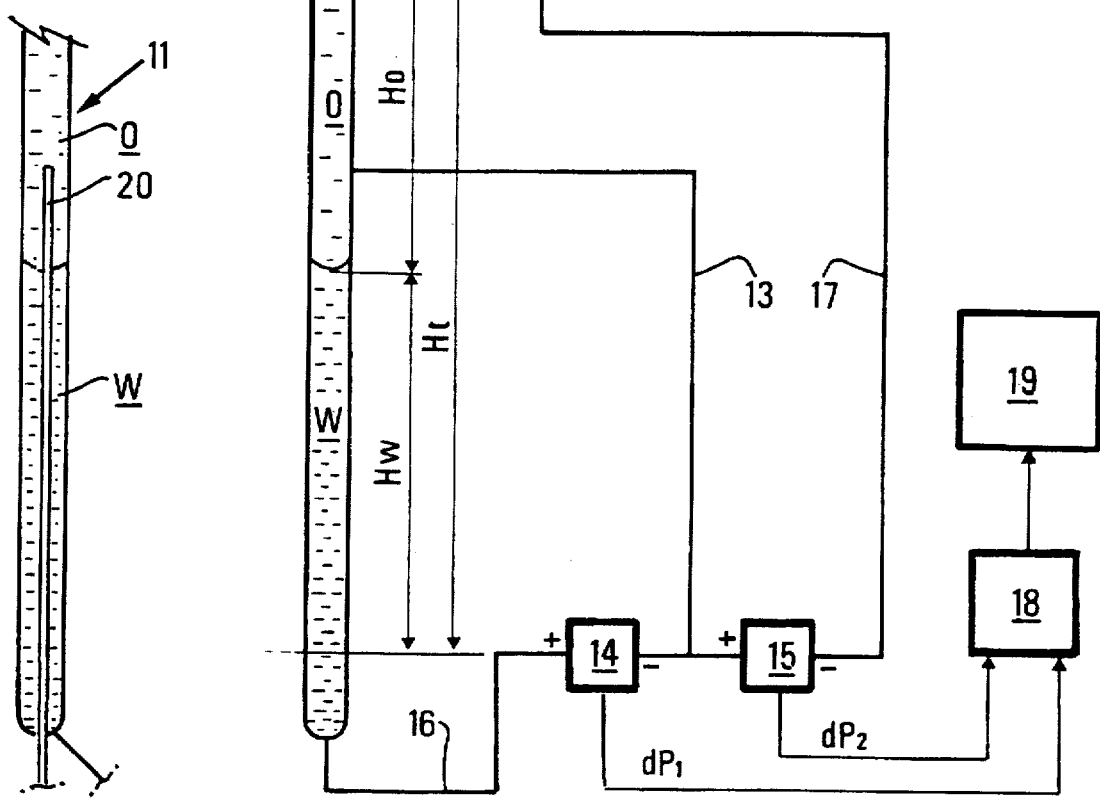
FIG. 2 shows an embodiment variant of the phase separator.

In the embodiment described above, the connection with the intermediate point of the column can be provided by a line exterior to the column. According to an embodiment variant schematized in FIG. 2, this connection can also be achieved by means of a fine tube 20 running through the bottom of the column and up to the intermediate level from the inside.

The measuring method according to the invention will be described hereafter in connection with fluid displacement operations for driving fluids out of a rock sample for example.

A dry porous sample for example is taken and saturated under vacuum with brine. A so-called SWI operation is carried out thereafter, which consists in injecting for example oil with a constant flow rate into the saturated sample by means of pump 9 until an irreducible minimum water-saturation level is reached.

Valve V2 is closed and, valve V4 being open, valves V1 and/or V3 are opened in order to inject water and/or gas for example through end plate 3 into the sample bar, 1 by means of pump 8. A mixture consisting of water, oil and gas, displaced by the injection, flows out through line 12 and enters separator 11. The different fluids separate by natural decantation. The oil accumulates in the intermediate pan of column of the separator 11, and the gas near the top thereof. HW and Ho respectively refer to the respective water and oil heights in the column, and Rw and Ro refer to the respective water and oil densities. In view of their respective connections with the different points of the column by lines 13 (or 20), 16, 17, the pressure detectors 14 and 15 measure respectively the differential pressures dP1 and dP2 which are expressed by the relations as follows:

$$dP1 = (Hw \cdot Rw + Ho \cdot Ro + Pg - Pc) - ((Hw + Ho) \cdot Ro + Pg - Pc) \quad (1)$$

$$dP2 = (Hw + Ho) \cdot Ro + Pg - Pc - (Pg - Pc) \quad (2)$$

where Pg refers to the pressure of the gas and Pc the pressure drop occurring on account of the presence of the flowmeter Q on the discharge pipe for discharging the gas out of the cell, these factors being eliminated as a result of the differential measurements.

The respective water and oil heights Hw and Ho are immediately deduced from these two relations at any time:

$$Hw = dP1 / (Rw - Ro) \quad (3)$$

$$Ho = (dP2 / Ro) - (dP1 / (Rw - Ro)) \quad (4),$$

and consequently also the respective water and oil volumes Hw.S and Ho.S expelled from the porous medium in column 11, the inner section S thereof being known.

The processor 18 is connected to the gas flowmeter D. It integrates the instantaneous flow rate values measured as a function of time so as to determine the volume of the gas phase entering the cell.

The respective water and oil volumes Vwi and Voi injected in the sample and the volume Vp of the pores of the sample tested being also known, the respective overall water and oil saturations Sw and So of the sample can be deduced therefrom with the relations:

$$Sw = (Vwi - Hw \cdot S) / Vp \text{ and } So = (Voi - Ho \cdot S) / Vp.$$

Processor 18 is programmed for example to compute automatically the volumes and the overall saturations from the above-defined relations, as well as the effective and relative permeabilities of the porous sample with respect to the fluids circulating therein.

The previous results remain of course valid in the absence of a third gas phase in the mixture expelled from the sample, the gas present in the column being then air at the atmospheric pressure.

The method has been described in an application intended to determine the respective volumes of the phases of a multiphase mixture expelled from a porous material bar. Without departing from the scope of the invention, the method described can also be applied to any mixture of fluid constituents having different densities and introduced in any vessel. This vessel can be a tube such as the column of the separator 11, above. However, the method according to the invention can apply more generally to any vessel: columns, tanks, etc, used for the storage or the transportation of fluid products, or for various process facilities, notably in the field of chemical engineering.

I claim:

1. A method for testing continuously physical characteristics of a sample of porous material saturated with a known volume of a mixture of different fluids having different densities by means of measurements performed on fluids drained progressively out of the sample and collected in an elongated phase separator comprising a column with a calibrated inner section arranged to obtain a vertical layering of the different phases, which method comprises, after vertical stratification of the collected fluids:

measuring a first pressure difference and a second pressure difference between a pressure prevailing at an intermediate height of the column and respectively a pressure prevailing near a closed base of the column and a pressure prevailing near the top of the column;

combining the first pressure difference and the second pressure difference to determine respective volumes of the collected fluids expelled from the sample; and determining from respective volumes of the different fluid and the known volume at least respective saturations of the sample by comparing the respective volumes with a known pore volume of the sample.

2. A device for testing continuously physical characteristics of a sample of porous material saturated with a known volume of a mixture of several fluids having different densities, by means of measurements performed on the fluids drained progressively out of the sample, comprising an elongated phase separator for collecting the mixture of fluids expelled from the sample, the separator comprising a column with a calibrated constant inner section arranged so as to obtain a vertical stratification of the different fluids, a first pressure means for measuring a pressure difference prevailing between a measuring point near the base of the column and an intermediate measuring point at an intermediate height of the column, and a second pressure means for measuring a pressure difference prevailing between the intermediate measuring point and a measuring point near the top of the column, and processing means including first means for combining the signals delivered by the first and second pressure measuring means in response to the measured pressure differences, in order to determine at least respective volumes of the different fluids expelled from the sample and determining physical characteristics from the respective volumes and the known volume, and second means for determining respective saturations of the sample by comparison of the respective volumes with a known pore volume of the sample.

3. A device as claimed in claim 2, wherein the first pressure means and the second pressure means are connected to the intermediate point of the column by means of a line exterior to the column.

4. A device as claimed in claim 2, wherein the first pressure means and the second pressure means are connected to the intermediate measuring point of the column by means of a line interior to said column.

5. A device as claimed in claim 2, wherein the processing means comprise a programmed processing set.

* * * * *